United States Patent [19]

Doan et al.

[11] Patent Number: 5,007,435
[45] Date of Patent: Apr. 16, 1991

[54] CONNECTOR FOR MULTICONDUCTOR PACING LEADS

[75] Inventors: Phong D. Doan, Shoreview; James E. Upton, New Brighton; Douglas N. Hess, Maple Grove; Wayne R. Bass, Coon Rapids; Keith A. Ufford, Maple Grove, all of Minn.

[73] Assignee: Medtronic, Inc., Minneapolis, Minn.

[21] Appl. No.: 513,461

[22] Filed: Apr. 23, 1990

Related U.S. Application Data

[62] Division of Ser. No. 198,540, May 25, 1988, Pat. No. 4,922,607.

[51] Int. Cl.⁵ .............................................. A61N 1/05
[52] U.S. Cl. ................................ 128/784; 128/419 P
[58] Field of Search ................... 128/642, 419 P, 784, 128/785, 786

[56] References Cited

U.S. PATENT DOCUMENTS

| | | | |
|---|---|---|---|
| 4,258,725 | 3/1981 | O'Neill | 128/419 P |
| 4,387,727 | 6/1983 | Sandstrom | 128/784 |
| 4,469,104 | 9/1984 | Peers-Trevarton | 128/419 P |
| 4,572,605 | 2/1986 | Hess | 339/177 R |
| 4,951,687 | 8/1990 | Ufford et al. | 128/786 |

FOREIGN PATENT DOCUMENTS 1146228  5/1983  Canada .................................. 337/70

Primary Examiner—William E. Kamm
Assistant Examiner—Scott M. Getzow

[57] ABSTRACT

A cardiac pacing lead having a plurality of individually insulated conductors arranged as a multifilar coil. The lead includes a connector assembly and a ring electrode assembly, each of which are optimized for use in conjunction with conductors arranged in the form of a multifilar coil. The connector assembly takes the form of an in-line connector having a plurality of linearly arranged connecting surfaces, each coupled to one of the conductors in the multifilar coil. The ring electrode assembly is constructed such that it displays the same outer diameter as the pacing lead. In both assemblies, conductors are coupled by means of welds, rather than by crimping or swaging.

7 Claims, 4 Drawing Sheets

CONNECTOR FOR MULTICONDUCTOR PACING LEADS

This is a divisional of application Ser. No. 198,540, filed on May 25, 1988, now U.S. Pat. No. 4,922,607.

BACKGROUND OF INVENTION

The present invention relates to medical electrical leads generally, and more particularly to cardiac pacing leads.

Early pacing leads, such as those disclosed in U.S. Pat. No. 3,348,548 and U.S. Pat. No. 3,788,329 employed separate conductor coils in a side-by-side or coaxial configuration, insulated from one another by plastic sheaths which covered the coils. More recently, multifilar coiled conductors having individually insulated coil wires have been pursued, as disclosed in Canadian Patent No. 1,146,228 for a MULTIPOLAR PACING CONDUCTOR, issued May 10, 1983 to Upton. This patent discloses a single, multiconductor DBS coil having individually insulated wires, and is incorporated herein by reference in its entirety.

SUMMARY OF THE INVENTION

The present invention is directed toward optimizing the construction of a pacing lead or other medical electrical lead of the type employing multiple, mutually insulated conductors, arranged in the form of a multipolar coil. In particular, the invention is directed toward improved connector assemblies and ring electrode assemblies for such leads.

Typically, in pacing leads employing a plurality of conductors, each of which are formed as a separate coil, connection of the coil to an electrode or a connector pin has been accomplished by means of crimping or swaging these components to one another, as disclosed in U.S. Pat. No. 4,258,725, issued to O'Neill and U.S. Pat. No. 4,328,812, issued to Ufford et al. However, where the conductors take the form of a multifilar coil, additional problems are presented. The conductors must be split off from the coil individually, and routed to the desired connector surface or electrode surface, without comprising the mechanical integrity of the lead at that point. Because one of the advantages of a multiconductor coil is that it allows fabrication of a smaller diameter lead, it is especially desirable to avoid unnecessary bulk in the vicinity of these assemblies.

The present invention addresses these problems by providing connector and electrode assemblies which are constructed to allow all electrical connections to the conductors to be made by welding. This allows for the elimination of crimping or swaging cores commonly used in prior art leads. In addition, the connector and ring electrode assemblies are designed to provide increased structural integrity and improved sealing due to the use of hot-melt and adhesive backfill procedures during manufacture.

DETAILED DESCRIPTION OF THE DRAWINGS

Figure 1:
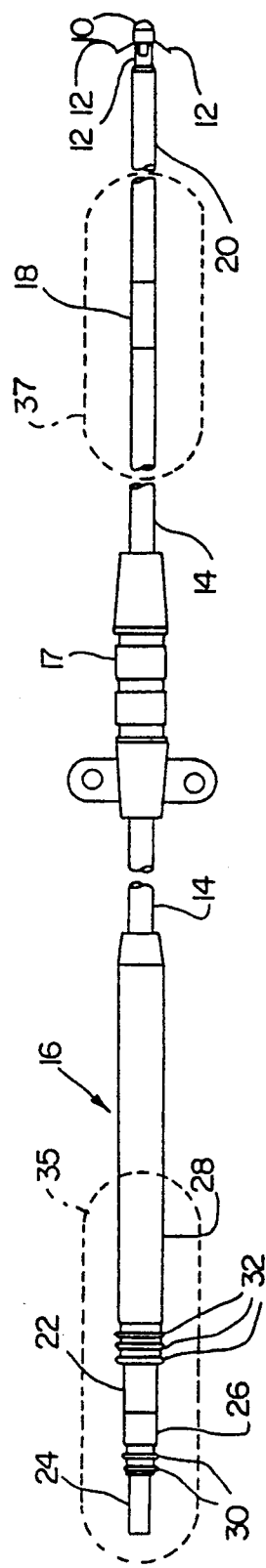
FIG. 1 shows a plan view of a bipolar cardiac pacing lead according to the present invention.

FIG. 1 is a plan view of a pacing lead employing improvements according to the present invention. At the distal end of the lead is located a pacing electrode 10, which may be fabricated according to any of a variety of well known electrode types. Preferably, the electrode is fabricated according to the disclosure in U.S. Pat. No. 4,506,680, issued to Stokes, and incorporated herein by reference in its entirety. Electrode 10 is held in place within the heart by means of pliant tines 12, which are more fully described in U.S. Pat. No. 3,902,501, issued to Citron et al, also incorporated herein by reference in its entirety.

The lead includes an elongated insulative sheath 14, which extends from the connector assembly 16 to the ring electrode 18. The lead also includes a second insulative sheath 20, extending from ring electrode 18 to electrode 10. Mounted around insulative sheath 14 is a suture sleeve 17, which is used to anchor the lead at the point of venous insertion. Connector assembly 16 includes a connector pin 24 and a connector ring assembly comprising an exposed ring shaped member 22. Insulative sleeve 26 separates pin 24 from ring member 22. Insulative sleeve 28 extends distal to ring member 22. The connector assembly is provided with resilient sealing rings 30 and 32, which seal the connector assembly within a corresponding receptacle mounted to a cardiac pacemaker. The area of the lead enclosed by dashed line 34 is illustrated in more detail in FIG. 2. The area of the lead enclosed by dashed line 36 is illustrated in more detail in FIG. 4.

Insulative sleeves 26 and 28 are preferably fabricated of silicone rubber. Insulative sheaths 14 and 20, are preferably fabricated of polyurethane or silicone rubber. Connector pin 24, ring member 22, ring electrode 18 and tip electrode 10 are preferably fabricated of inert conductive metals such as platinum, Elgiloy ® alloy, MP35N or stainless steel.

Figure 2:
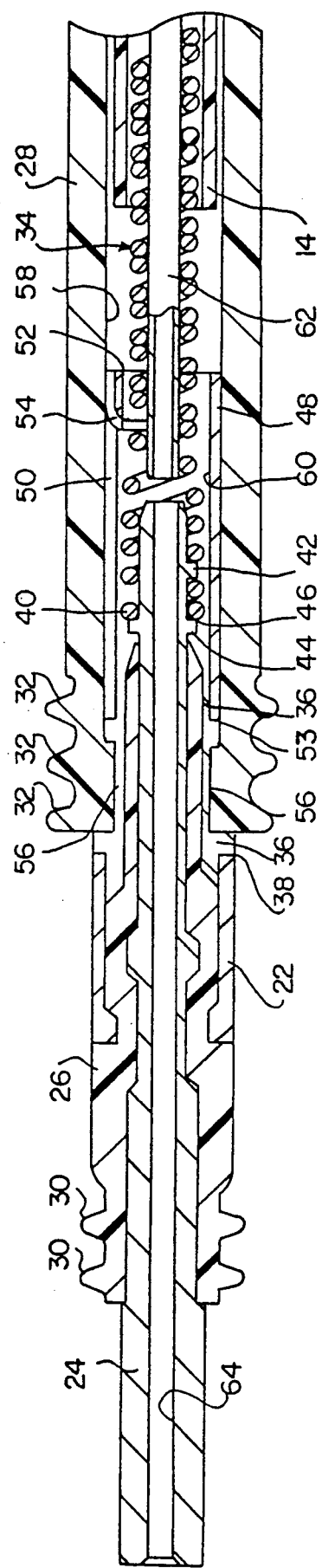
FIG. 2 shows a sectional view of the lead of FIG. 1 in the vicinity of the connector assembly.

FIG. 2 shows a sectional view of the proximal portion of connector assembly 16, illustrated in FIG. 1. This view shows the interconnection of the multiconductor coil 34 with the other components of connector assembly 16, illustrated in FIG. 1. Components visible in FIG. 1 are labeled similarly in FIG. 2. Multiconductor coil 34 includes a first coiled conductor coupled to connector pin 24 and a second coiled conductor electrically coupled to ring member 22.

The connector assembly is fabricated by first laser welding ring member 22 to cylindrical member 36 by means of a circumferential laser weld at 38 to form a connector ring assembly. Assembled ring member 22 and cylindrical member 36 are assembled over connector pin 24, placed into a mold, and insulative sleeve 26 is then injection molded between them. This process is disclosed in more detail in U.S. Pat. No. 4,572,605, issued to Hess and incorporated herein by reference in its entirety.

The completed assembly of connector pin 24, insulative sleeve 26, ring member 22 and tubular member 36 is then coupled to one conductor 40 of multiconductor coil 34. Conductor 40 is screwed onto the distal end of connector pin 24, with protrusion 42 acting as a screw thread. Conductor 40 is screwed onto connector pin 24 until its proximal end butts up against circular flange 44. Conductor 40 is then coupled to circular flange 44 at 46 by means of a spot laser weld. The spacing intermediate circular flange 44 and protrusion 42 allows for a limited amount of strain relief immediately distal to the spot laser weld at 46.

Tubular extension 48, which takes the form of a cylinder having an extended longitudinal slot 50 is then slid over the distal end of cylindrical member 36 and coupled to it by means of a circumferential laser weld at 52. A shallow grooved section 52, having a groove that corresponds generally to the size of conductor 54, is located at the proximal end of slot 50 in tubular extension 48. Conductor 54 is stripped of insulation and laid lengthwise in the grooved area 52, and laser welded to extension 48. Following this step, insulative sleeve 28 is slid over extension 48 and over cylindrical member 36. Member 36 is provided with a cross bore 56, which may be filled with medical adhesive, thereby bonding insulative sleeve 28 to insulative sleeve 26.

Finally, the entire assembly is backfilled with adhesive injected between insulative sheath 14 and insulative sleeve 28, filling the area between insulative sleeve 28 and sheath 14, as well as the lumen 58 of sleeve 28 and the lumen 60 of tubular extension 48. This serves to bond the components of the connector assembly to one another and to insulative sleeve 28 and to electrically insulate the conductor 40 and connector pin 24 from the conductor 54. For the sake of clarity, the backfilled adhesive is not shown in this illustration. Mounted within multiconductor coil 34 is a Teflon ® plastic liner 62, which serves as a passageway for a stylet. The internal lumen of liner 62 is aligned with the internal bore 64 of connector pin 24.

Figure 3:
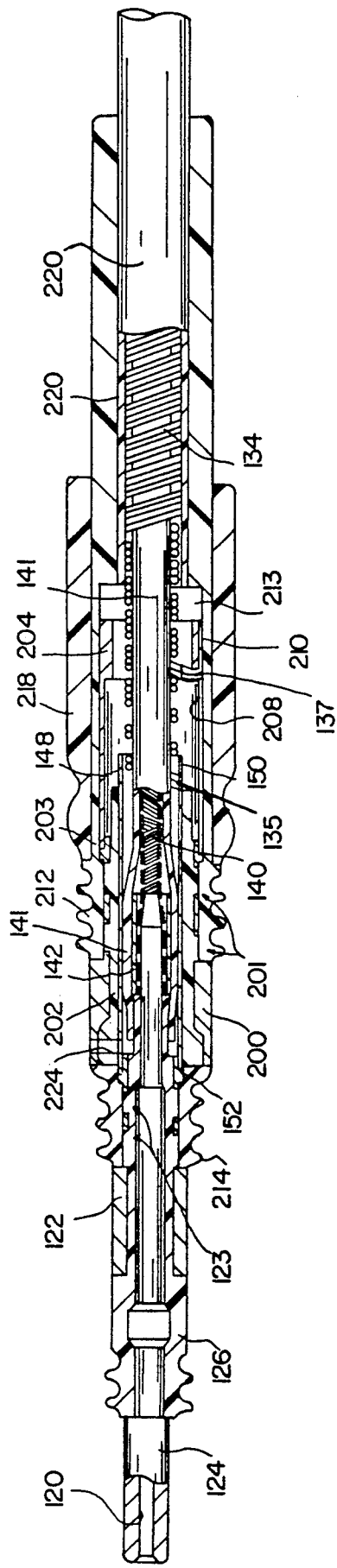
FIG. 3 shows an alternative connector assembly for use with a tripolar lead.

FIG. 3 shows an alternative connector assembly adapted for use with a tripolar, coaxial lead. This figure illustrates how sequential application of the basic techniques disclosed in conjunction with the bipolar lead can be used to produce a tripolar or multipolar connector having sequential, ring shaped connector surfaces.

The connector assembly of FIG. 3 is fabricated by first assembling connector ring 122 over connector pin 124, placing them in a mold and subsequently injection molding insulative sleeve 126 between them. This process is disclosed in the above cited Hess patent. Connector pin 124 is provided with a lumen 120 through which a stylet may be inserted. Connector ring 122 is provided with two perpendicular bores 123 which are filled by sleeve 126 during the molding procedure. The assembly of connector pin 124, sleeve 126 and connector ring 122 is then coupled to the inner conductor coil 140. Conductor coil 140 is slipped over the distal end of connector pin 124, and held in place by means of crimping sleeve 142. Insulative sleeve 141 is then slid over inner conductor 140.

After attachment of inner conductor 140 to the distal end of connector pin 124, tubular extension 148, which takes the form of a cylinder having a longitudinal slot 150 at its distal end and second connector ring 200 are assembled in their respective positions in an injection mold, and insulative sleeve 202 is injection molded between them. Connector ring 200 is provided with two perpendicular bores 201 which are filled by sleeve 202 during the molding process. This assembly is then slid over the distal end of connector ring 122 and coupled to it by means of a circumferential laser weld at 152. After this step, the proximal ends of two of the individual conductor wires 135 of multifilar coil 134 are stripped of insulation and laser welded to tubular extension 148 in slot 150. Following this step, a second tubular extension 204 is slid over tubular extension 148. Second tubular extension 204 is welded to second connector ring 200 by means of a circumferential laser weld at 203. Tubular extension 204 includes an elongated slot 208 and a shallow grooved section 210 at its distal end. The proximal ends of the two other conductors 137 from multipolar coil 134 are stripped, laid in shallow groove 210 and laser welded within groove 210. Outer insulative sheath 220 is then slid over multipolar coil 134.

After these steps have been completed, a sealing ring/strain relief member 212 is applied around the second connector ring 200. Because of the penetration of the material of sleeve 202 through bores 201, member 212 can be bonded directly to insulating sleeve 202 using a suitable adhesive. This provides a better bond than would be available if member 212 were bonded directly to connector ring 200. If sleeve 202 and sealing ring member 212 are both fabricated of silicone rubber, a silicone medical adhesive would be appropriate.

The interior of the assembly is backfilled with silicone adhesive 222 through bore 224, which extends through second connector ring 200, sleeve 202 and tubular extension 148. Backfilling continues until the adhesive is visible within the lumen of sealing ring/strain relief member 212, distal to tubular extension 204. This seals the lead, provides additional electrical insulation, and internally bonds the components together for added mechanical strength.

A second sealing ring member 214 is applied exterior to first connector ring 122. Because sleeve 126 extends through bores 123, sealing ring member 214 may be bonded directly to sleeve 126, using a suitable adhesive.

Surrounding sealing ring strain relief member 214 is a locking sleeve 218, which is intended to be used in conjunction with a deflectable beam locking member on the connector housing into which the lead is inserted. This connector system is disclosed in more detail in copending, commonly assigned U.S. patent application Ser. No. 184,903, for IN-LINE PACEMAKER CONNECTOR SYSTEM, filed Apr. 22, 1988, by Terry Daglow and Richard Sandstrom, and incorporated herein by reference in its entirety.

Connector rings 122 and 200, connector pin 124, tubular extensions 148 and 204 and crimp sleeve 142 may all be fabricated of an inert, biocompatible metal such as stainless steel. Sleeves 126 and 202 and sealing ring members 212 and 214 are preferably fabricated of silicone rubber. Sheaths 141 and 220 and locking sleeve 218 are preferably fabricated of polyether urethane.

By repeated duplications of the connector rings, insulating sleeves and tubular extensions, a connector assembly having any number of linearily arranged connector rings may be produced. The particular configuration of the components allows for the use of laser or resistance welding to accomplish all metal to metal connections, leading to increased reliability and improved reproducibility during production. Therefore, both the method of fabrication of this connector assembly and the resultant product are believed to be a substantial improvement over previous in-line connector designs.

Figure 4:
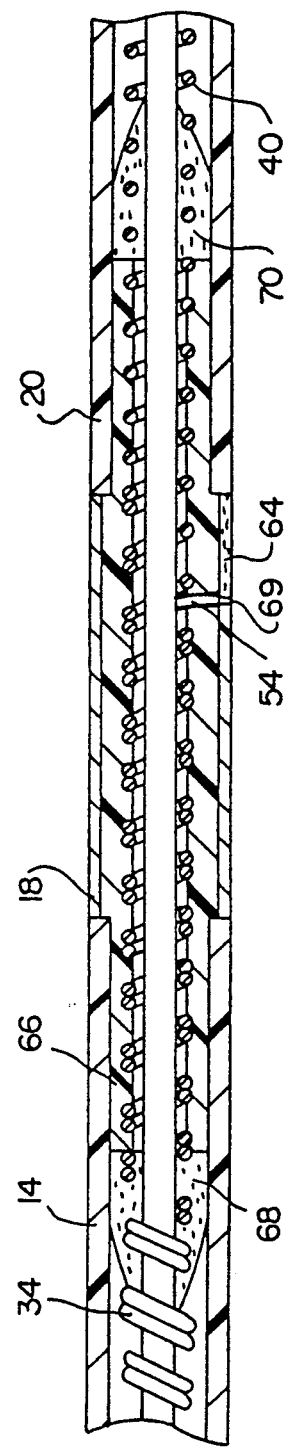
FIG. 4 shows a sectional view of the lead of FIG. 1 in the vicinity of the ring electrode.

FIG. 4 shows a sectional view of the area adjacent the ring electrode 18, illustrated in FIG. 1. In this view, the interconnection of the conductor 54 and ring electrode 18 is illustrated. Ring electrode 18 takes the form of a metal cylindrical tube, having a slot 64 adjacent its distal end. The stripped end of conductor 54 is laser welded to the end of slot 64 in electrode 18 at 66. This provides the electrical connection between the conductor and the ring electrode. The mechanical connection between the various parts of the electrode is provided by means of a plastic sleeve 66, which is preferably fabricated of Pellethane ® 2363-80A polyether urethane. Pellethane ® 2363-55D polyether urethane may also be used.

The ring electrode 18 is accomplished by first sliding sleeve 66 over the multifilar coil 34. Conductor 54 is brought out through a hole in sleeve 66. Then the assembly of coil 34 and sleeve 66 is inserted into a cylindrical mold having a diameter slightly less than the inner diameter of the ring electrode 18. Heat is applied, causing the insulative sleeve to heat bond to multifilar coil 34. This also causes sleeve 66 to flow between the conductors of multifilar coil 34, stabilizing it in the area of the electrode. Ring electrode 18 is slid over sleeve 66, and the stripped end of conductor 54 is laser welded to ring electrode 18 at 69. At the ends of sleeve 66, medical adhesive 68 and 70 is provided, bonding the insulative sleeve 66 to the multifilar coil 34 and to the liner 62. This structure provides mechanical integrity to the assembly and acts as a strain relief. Insulative sheaths 14 and 20 are then slid over the ends of insulating sleeve 66, and the assembly is inserted into a cylindrical mold having a diameter corresponding to the outer diameter of ring electrode 18. Heat is applied, causing insulative sleeve 66 to heat bond to ring electrode 18 and to insulative sleeves 14 and 20. The resultant structure provides a lead having a uniform outer diameter in the vicinity of the ring electrode. The bonding of sleeve 66 to sheaths 14 and 20 provides a continuous electrically insulative and fluid tight tube which extends the length of the lead. During heating, sleeve 66 also collapses around conductor 54, sealing this potential point of fluid entry as well. Slot 64 in ring electrode 18 is filled with medical adhesive 70, to complete the assembly. In order to improve the mechanical interconnection of the components of the lead, the Tefzel ® plastic insulation of the multiconductor coil 34 and Teflon ® plastic tubing 62 are treated with Chemgrip or by glow discharge (plasma) to activate their surfaces to enhance adhesion to the sleeve 66 and to silicone medical adhesive 70. A polyurethane glue, comprised of Pellethane ® 2363-75D in N,N-dimethyl acetamide, is applied to the sleeve 66 and subsequently air dried to enhance adhesion to silicone medical adhesive. Adhesion promoters, such as Dow Corning ® Z-6020 silane (amino alkyl functional silane), may be applied to metal or plastic components prior to the application of medical adhesive to further improve the mechanical interconnection of the lead components.

The resulting assembly provides a structure which is tightly sealed against fluid entry, and which displays a high tensile strength through the area of the ring electrode. This structure also provides a gradual transition in flexibility from the ring electrode 18 proximally and distally, through the combination of sleeve 66 and adhesive 68 and 70. In addition, the structure allows for the fabrication of a substantially smaller diameter ring electrode than possible using assemblies which require crimping or swaging cores, as disclosed in U.S. Pat. No. 4,328,812, issued to Ufford et al, discussed above.

Although the particular embodiment disclosed in this application takes the form of a cardiac pacing lead, the inventions disclosed herein are believed equally applicable to medical electrical leads in general. In conjunction with the above description, we claim:

1. A connector pin assembly, comprising:
   an elongated conductive connector pin having a proximal end and a distal end;
   a first insulative sheath coaxially mounted around said connector pin, said first insulative sheath terminating proximal to the distal end of said connector pin;
   first connector ring mounted around said first insulative sheath, said first connector ring having a proximal end a distal end, the distal end of said first connector ring terminating proximal to the distal end of said connector pin;
   a first conductive extension electrically and mechanically coupled to the distal end of said connector ring and extending distally therefrom;
   a first electrical conductor coupled to the distal end of said connector pin; and
   a second conductor electrically and mechanically coupled to the distal end of said extension.

2. A connector assembly according to claim 1 further comprising an outer, insulative sheath extending distally from said connector ring, enclosing the distal end of said first connector ring, said first extension and said first and second conductors.

3. A connector assembly according to claim 1 or claim 2 further comprising an adhesive back-filled between and coupled to said connector pin and said first extension.

4. A connector assembly according to claim 1, further comprising a second insulative sleeve mounted to and surrounding the distal end of said first connector pin and the proximal portion of said extension;
   a second connector ring mounted to and surrounding the distal portion of said second insulative sleeve, said second connector ring having a proximal end and a distal end;
   a second conductive extension coupled to the distal end of said second connector ring and extending distally therefrom; and
   a third electrical conductor electrically and mechanically coupled to the distal end of said second extension.

5. A connector assembly according to claim 4, further comprising an insulative sheath enclosing said second extension and said first, second and third conductors.

6. An implantable electrical lead, comprising:
   first and second mutually insulated elongated conductors having proximal and distal ends;
   a first elongated insulative sheath covering said first and second conductors; and
   a connector pin assembly mounted to the proximal end of said first and second conductors, comprising:
      a connector pin having a proximal end and a distal end;
      a second insulative sheath mounted around said connector pin, terminating proximal to the distal end of said connector pin and terminating distal to the proximal end of said connector pin;
   a connector ring mounted around said connector pin and said second insulative sheath, said connector ring terminating proximal to the distal end of said connector pin and distal to the proximal end of said first insulative sheath;
   a conducive extension coupled to said connector ring, extending distally from said connector ring to a point distal to the distal end of said connector pin; and a third insulative sheath extending distally from said connector ring and enclosing said conductive extension; and wherein said first and second conductors are electrically coupled to the distal end of said connector pin and to said conductive extension, respectively.

7. An implantable electrical lead according to claim 6 wherein said second insulative sheath is provided with at least one sealing ring extneding outwardly from said second insulative sheath, proximal to said connector ring; and wherein said third insulative sheath includes at least one sealing ring extending outwardly from said third insulative sheath distal to said connector ring.

* * * * *